(12) United States Patent
Tawil et al.

(10) Patent No.: US 10,849,944 B2
(45) Date of Patent: Dec. 1, 2020

(54) MICROENCAPSULATION OF BACTERIOPHAGES AND RELATED PRODUCTS

(71) Applicant: PHAGELUX (CANADA) INC., Montreal (CA)

(72) Inventors: Nancy Tawil, Cantley (CA); Edwige Caroline Rebecca Arnold, Montreal (CA); Ramaz Katsarava, Tbilisi (GE); David Tugushi, Tbilisi (GE); Vakhtang Beridze, Tbilisi (GE)

(73) Assignee: PHAGELUX (CANADA) INC., Montreal (CA)

( * ) Notice: Subject to any disclaimer, the term of this patent is extended or adjusted under 35 U.S.C. 154(b) by 0 days.

(21) Appl. No.: 16/310,732

(22) PCT Filed: Jun. 22, 2017

(86) PCT No.: PCT/IB2017/053744
§ 371 (c)(1),
(2) Date: Dec. 17, 2018

(87) PCT Pub. No.: WO2017/221201
PCT Pub. Date: Dec. 28, 2017

(65) Prior Publication Data
US 2019/0247451 A1 Aug. 15, 2019

Related U.S. Application Data
(60) Provisional application No. 62/353,658, filed on Jun. 23, 2016.

(51) Int. Cl.
| | | |
|---|---|---|
| *A61K 47/30* | (2006.01) | |
| *A61K 47/34* | (2017.01) | |
| *A61K 9/50* | (2006.01) | |
| *A61K 35/76* | (2015.01) | |
| *A61K 9/06* | (2006.01) | |
| *A61K 9/12* | (2006.01) | |
| *A61K 9/70* | (2006.01) | |
| *A61K 9/08* | (2006.01) | |
| *A61K 45/06* | (2006.01) | |
| *A61K 47/32* | (2006.01) | |

(52) U.S. Cl.
CPC ............. *A61K 35/76* (2013.01); *A61K 9/06* (2013.01); *A61K 9/08* (2013.01); *A61K 9/12* (2013.01); *A61K 9/5031* (2013.01); *A61K 9/7015* (2013.01); *A61K 45/06* (2013.01); *A61K 47/30* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | |
|---|---|---|
| 5,710,233 A | 1/1998 | Meckel et al. |
| 6,503,538 B1 | 1/2003 | Chu et al. |
| 6,703,040 B2 | 3/2004 | Katsavara et al. |
| 7,304,122 B2 | 12/2007 | Chu et al. |
| 7,408,018 B2 | 8/2008 | Chu et al. |
| 7,649,022 B2 | 1/2010 | Gomurashvili et al. |
| 7,794,706 B2 | 9/2010 | Carpenter et al. |
| 7,863,406 B2 | 1/2011 | Chu et al. |
| 7,910,086 B1 | 3/2011 | Sung et al. |
| 8,445,627 B2 | 5/2013 | Katsarava et al. |
| 8,715,740 B2 | 5/2014 | Wang et al. |
| 2006/0024357 A1 | 2/2006 | Carpenter et al. |
| 2006/0177416 A1* | 8/2006 | Turnell .................. A61P 19/06 424/78.27 |
| 2006/0286064 A1 | 12/2006 | Turnell et al. |
| 2007/0106035 A1 | 5/2007 | Gomurashvili et al. |
| 2009/0130196 A1* | 5/2009 | Murthy ................ A23K 20/195 424/451 |
| 2010/0040664 A1 | 2/2010 | Katsarava et al. |
| 2016/0279070 A1 | 9/2016 | Gorecka et al. |
| 2016/0375139 A1 | 12/2016 | Katsarava et al. |

FOREIGN PATENT DOCUMENTS

| | | |
|---|---|---|
| CA | 2649672 | 11/2007 |
| GE | P 2012 5618 B | 8/2012 |
| WO | 2015084938 | 6/2015 |

OTHER PUBLICATIONS

Written Opinion of the International Searching Authority issued by the World Intellectual Property Organization dated Sep. 28, 2017 for PCT application PCT/IB2017/053744 from which the present application is a national phase.

International Search Report issued by the World Intellectual Property Organization dated Sep. 28, 2017 for PCT application PCT/IB2017/053744 from which the present application national phase.

Puapermpoonsiri U et al. "A freeze-dried formulation of bacteriophage encapsulated in biodegradable microspheres.", May 2009 Eur J Pharm Biopharm.;72(1):26-33.

Stanford K1, McAllister TA, Niu YD, Stephens TP, Mazzocco A, Waddell TE, Johnson RP. Stanford K. et al., "Oral delivery systems for encapsulated bacteriophages targeted at *Escherichia coli* O157:H7 in feedlot cattle.", Jul. 2010, J Food Prot.;73(7):1304-12.

Ahmed S Abdulamir et al., "Novel approach of using a cocktail of designed bacteriophages against gut pathogenic *E. coli* for bacterial load biocontrol", Jul. 2014, Annals of Clinical Microbiology and Antimicrobials , 13(1):39.

(Continued)

*Primary Examiner* — Brian Gulledge

(57) ABSTRACT

An encapsulated bacteriophage formulation and a method for encapsulating bacteriophages and bacteriophage-related products in polymeric microcapsules is provided. Some embodiments of the method of producing the encapsulated bacteriophages involves a water-in-oil-in-water double emulsion.

27 Claims, 3 Drawing Sheets

(56) References Cited

OTHER PUBLICATIONS

Markoishvili K. et al., "A novel sustained-release matrix based on biodegradable poly(ester amide)s and impregnated with bacteriophages and an antibiotic shows promise in management of infected venous stasis ulcers and other poorly healing wounds.", Jul. 2002, Int J Dermatol.;41(7):453-8.
Patricia Perez Esteban et al., "Enhancement of the antimicrobial properties of bacteriophage-K via stabilization using oil-in-water nano-emulsions", Apr. 2014, American Institute of Chemical Engineers Biotechnol. Prog., 30:932-944.
Korehei R. et al. May 2013, "Incorporation of T4 bacteriophage in electrospun fibres.", J Appl Microbiol.;114(5):1425-34.
Translation of Georgian Patent P 2012 5618 B, cited in "Foreign Patent Documents" section.

\* cited by examiner

MICROENCAPSULATION OF BACTERIOPHAGES AND RELATED PRODUCTS

FIELD OF THE INVENTION

The present invention relates to the general field of bacteriophages and is more particularly concerned with microencapsulation of bacteriophages and related products.

BACKGROUND

Multidrug and pandrug-resistant bacteria pose a major threat to human, animal and plant health. Multidrug resistant strains of bacteria such as *Staphylococcus aureus* and *Pseudomonas aeruginosa* play a prominent role as an etiological agent of serious nosocomial and community acquired infections. These infections often lead to bacteremia, sepsis, and high rate of mortality and morbidity.

Hence, the development of new therapeutic and prophylactic strategies for the control of bacterial infections in human patients, livestock, and produce is needed.

An alternative or supplement to antibiotic therapy is the use of bacteriophages to target bacterial infections. Advantages of phage therapy resides in the bactericidal effect of phages, their auto-dosing ability by proliferating locally in areas infected by their bacterial host, their low inherent toxicity, their minimal disruption of the normal bacterial flora and microbiome, their synergy with antibiotics, the cocktail formulation versatility and their ability to clear biofilms. Reports of successful bacteriophage therapy have been extensively reviewed. Clinical use of bacteriophages often involve the delivery of naked phages in simple liquid formulations. The effectiveness of phage therapy can be affected by multiple factors such as lack of specificity of the phage to the target infection, rapid clearance by the immune system, inactivation by unfavorable environmental factors such as adverse enzymes, pH, and temperature and long term storage. In view of this, administration of phages in human and animals requires an appropriate delivery system.

Although a number of advanced methods for controlled and or targeted drug delivery have been trying to build on the conventional drug delivery method of microencapsulation proposed in the 1960s, these techniques have not addressed the growing need of encapsulating bacteriophages with maximal efficiency in biodegradable polymeric microcapsules. For example, liposomes are not suited for delivering phages are they are thermodynamically unstable, and tend to fuse, resulting in the early release of the therapeutic agent. Phages have also been encapsulated in alginate, chitosan, and pectin, (with mitigated results) with loss of lytic activity of the phages and such formulations do not provide sufficient protection again stomach acidity, and do not show long term stability of the formulations. Moreover, phages have been encapsulated in poly (DL-lactic co-glycolic acid) (PGLA), but this resulted in loss of stability and integrity of the bacteriophages after 7 days due to the physical interaction at the surface or encapsulation within the PGLA porous matrix.

Accordingly, there exists a need for a new ways to encapsulate bacteriophages.

SUMMARY OF THE INVENTION

Novel amino acid based biopolymers are easy to produce, have low cost, maintain phage viability, are stable, do not cause immunogenic reactions, are biodegradable, allow for high phage loading and have a proper phage release rate.

Incorporating phages into biodegradable amino acid-based microparticles would be beneficial for many reasons, including protection from denaturation and inactivation, as well as enhanced therapeutic activity that prolong the release and presence of the phage in the human body. Other advantages of encapsulating phages into microparticles reside in increased circulation time of phages, decreased systemic clearance, protection from enzymatic or acidic degradation, and controlled release.

The present invention proposes methods for encapsulating bacteriophages and compositions prepared using such methods. Possible uses for the invention include local delivery on skin, ears, throat, nose, pulmonary delivery, mucosal membranes, vagina, burns, ulcers (pressure, venous, diabetic, etc.), surgical wounds, other types of wounds. Are also contemplated intramuscular delivery, subcutaneous deliver, oral or intraoeritonial delivery. The proposed compositions are also usable for reducing pathogen colonization in livestock, biocontrol of raw meats and fresh products, biopreservation and expansion of shelf life of ready products.

The present invention relates to encapsulating bacteriophages into polymeric microparticles. In particular this invention pertains to encapsulating bacteriophage, bacteriophage products, or phage-related products, such as endolysins, lysostaphins, phage proteins or phage enzymatic formulations and the methods of preparing compositions incorporating these encapsulations. The water-based formulations provide a mean for the controlled release of bacteriophages for different bacterial targets.

The invention is based on encapsulated phages in microcapsules made of a suitable polymer, such as a Polyester amide urea (PEAU), a leucine-based poly ester amide polymer, or another amino acid based copolymer. Due to both groups, ester and amide, such polymers are biodegradable (ester group) and have good thermal stability and mechanical strength (amide group with strong intermolecular interactions). The incorporation of leucine, or other suitable amino acid, improves the biocompatibility of the polymer. The biodegradation rate of this polymer can easily be adjusted by changing its exact composition and molecular weight. When microcapsules are formed, the liberation rate of any product incorporated therein can be adjusted by controlling the size and thickness of the microcapsules.

Such a polymer is synthesized, in some embodiments, by interfacial polycondensation of the monomer L6, di-p-sulfonic acid salt of bis-(L-leucine)-1,6-hexylene diester with trisphogene/sebacoyl chloride with water/dichloromethane system. The use of dichloromethane allows direct utilization of the biocomposite for phages incorporation therefore for microcapsules fabrication. This method is fast, irreversible, involves two immiscible phases at room temperature and lead to high molecular weight polymer. Synthesis of the monomer L6 was executed in the presence of p-toluene sulfonic acid by condensation of L-leucine with 1,6-hexanediol in refluxed cyclohexane, because it is less toxic than solvents such as benzene. Purification includes recrystallization from water, filtration and drying under vacuum.

The formulations containing microcapsules are fabricated using a water-in-oil-in-water double emulsion-solvent where the addition of the bacteriophages occurs in some embodiments in the secondary emulsion to minimize their exposure with the solvent dichloromethane (DCM). The DCM can also be replaced by an other suitable solvent, such as ethyl acetate, chloroform, or another organic solvent. Bacteriophages are stable against DCM, especially during the time of the reaction. It was found that, in some embodiments, there is no need to use a hardening tank during preparation of the microcapsules. Hardening tanks require dilution of the microcapsule preparation, for example by a factor of 5 or more. In addition to requiring additional processes to recover the microcapsules in the relatively large volume of liquid, use of hardening tank results in dilution of any component left in the aqueous phase in which the microcapsules are suspended, such as bacteriophages.

Other polymers usable in the invention include:
A polymer selected from
(1) a poly (ester amide urea) wherein at least one diol, at least one diacid, and at least one amino acid are linked together through an ester bond, an amide bond, and a urea bond,
(2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond,
(4) a poly (ester amide urethane) wherein at least one diol, at least one diacid, and at least one amino acid are linked together through an ester bond, an amide bond, and a urethane bond,
(5) a poly (ester urea) wherein at least one diol and at least one amino acid are linked together through an ester bond and a urea bond, and
(6) a poly (ester urethane) wherein at least one diol and at least one amino acid are linked together through an ester bond and a urethane bond, further wherein
the at least one diol is a compound of formula:
HO—$R_1$—OH, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

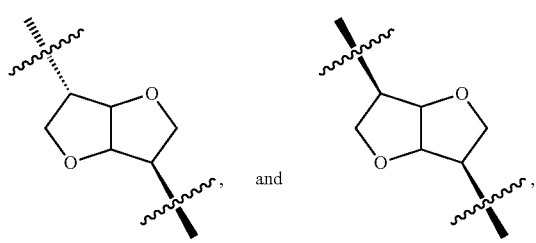, and the at least one diacid is a compound of formula:
HO—(CO)—$R_3$—(CO)—OH, $R_3$ is $C_2$-$C_{12}$ alkylene,
the at least one amino acid is chosen from naturally occurring amino acids and non-naturally occurring amino acid.

In some embodiments, the polymer is selected from
(1) a poly (ester amide urea) wherein at least one diol, at least one diacid, and at least one amino acid are linked together through an ester bond, an amide bond, and a urea bond,
(2) a poly (ester urethane urea) wherein at least one diol and at least one amino acid are linked together through an ester bond, a urethane bond, and a urea bond,
(3) a poly (ester amide urethane urea) wherein at least one diol, at least one diacid, and at least one amino acid are linked together through an ester bond, an amide bond, a urethane bond, and a urea bond, and
(4) a poly (ester amide urethane) wherein at least one diol, at least one diacid, and at least one amino acid are linked together through an ester bond, an amide bond, and a urethane bond, wherein the at least one diol, at least one diacid, and at least one amino acid are as defined in claim 1.

In some more specific embodiments of the invention, the polymer is a poly (ester amide urea) comprising the following two blocks with random distribution thereof:

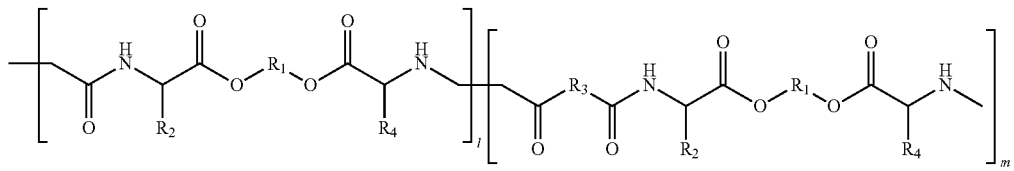

wherein
the ratio of l:m ranges from 0.05:0.95 to 0.95:0.05, l+m=1,
$R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes,

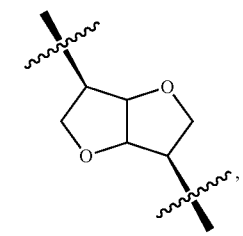

$R_3$ is $C_2$-$C_{12}$ alkylene,
$R_2$ and $R_4$ are independently chosen from the side chains of L- and D-amino acids so that the carbon to which $R_2$ or $R_4$ is attached has L or D chirality.

In some more specific embodiments of the invention, the polymer is poly (ester urethane urea) comprising the following two blocks with random distribution thereof:

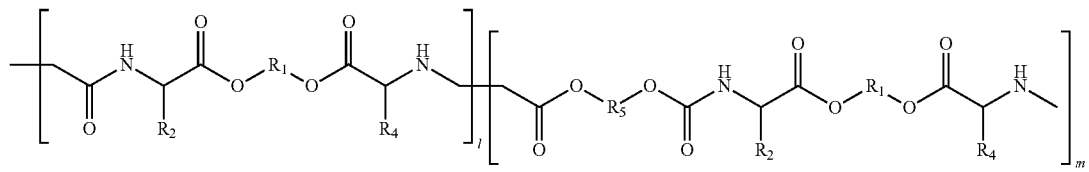

wherein
the ratio of l:m ranges from 0.05:0.95 to 0.95:0.05, l+m=1,
$R_1$ and $R_5$ are independently chosen from $C_2$-$C_{12}$ alkylenes optionally interrupted by at least one oxygen, $C_3$-$C_8$ cycloalkylenes, $C_3$-$C_{10}$ cycloalkylalkylenes,

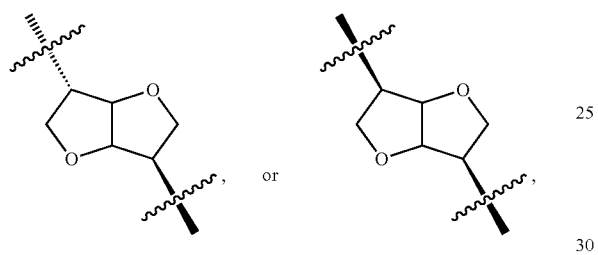

or and
$R_2$ and $R_4$ are independently chosen from the side chains of L- and D-amino acids so that the carbon to which $R_2$ or $R_4$ is attached has L or D chirality.

In some more specific embodiments of the invention, the polymer is poly (ester amide urethane urea) comprising the following three blocks with random distribution thereof:

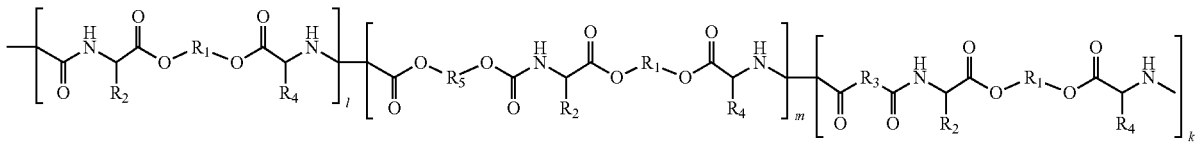

wherein
the ratio of l:m:k ranges from 0.05:0.05:0.90 to 0.90:0.05:0.05, l+m+k=1, $R_1$ and $R_5$ are independently chosen from $C_2$-$C_{12}$ alkylenes optionally interrupted by at least one oxygen, $C_3$-$C_8$ cycloalkylenes, $C_3$-$C_{10}$ cycloalkylalkylenes,

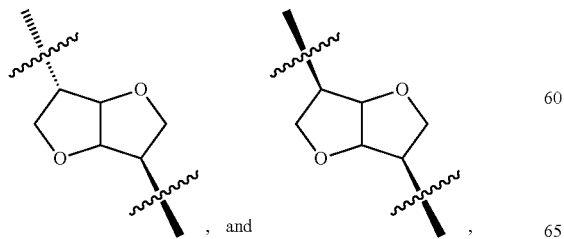

, and $R_3$ is $C_2$-$C_{12}$ alkylene, and $R_2$ and $R_4$ are independently chosen from the side chains of L- and D-amino acids so that the carbon to which $R_2$ or $R_4$ is attached has L or D chirality.

In some more specific embodiments of the invention, the polymer is (ester amide urethane) comprising the following two blocks with random distribution thereof:

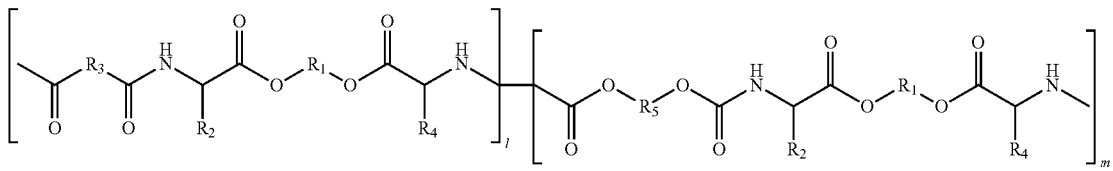

wherein
the ratio of l:m ranges from 0.05:0.95 to 0.95:0.05, l+m=1, $R_1$ and $R_5$ are independently chosen from $C_2$-$C_{12}$ alkylenes optionally interrupted by at least one oxygen, $C_3$-$C_8$ cycloalkylene, $C_3$-$C_{10}$ cycloalkylalkylene,

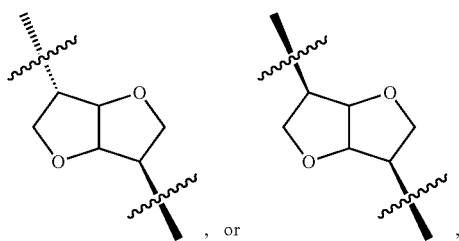

, or , $R_3$ is $C_2$-$C_{12}$ alkylene, and $R_2$ and $R_4$ are the same and selected from the side chains of L- and D-amino acids so that the carbon to which $R_2$ or $R_4$ is attached has L or D chirality.

In the above polymers, in some very specific embodiments of the invention, one or more of the following hold: $R_1$ is —$(CH_2)_6$—, $R_3$ is —$(CH_2)_8$—, or both $R_2$ and $R_4$ are the side chain of L-leucine.

Blends of the above-mentioned polymers are also usable in the preparation of the compositions of the present invention. More details regarding such polymers and others usable with the present invention are provided in PCT application PCT/US2016/038527 and U.S. patent application Ser. No. 15/188,783, the contents of which is hereby incorporated by reference in its entirety. The present application claims priority from U.S. provisional patent application 62/353,658 filed Jun. 23, 2016, the contents of which is hereby incorporated by reference in its entirety.

In a broad aspect, the invention provides a composition including: polymer microcapsules; at least one of active bacteriophages and bacteriophage related products encapsulated in the polymer microcapsules; wherein the polymer microcapsules include an amino-acid based polymer.

The invention may also provide a composition wherein active bacteriophages are encapsulated in the polymer microcapsules.

The invention may also provide a composition wherein the active bacteriophages are in a first aqueous suspension in the polymer microcapsules.

The invention may also provide a composition wherein the first aqueous suspension includes polyvinyl alcohol.

The invention may also provide a composition wherein the first aqueous suspension includes between 0.1% and 10% w/v of the polyvinyl alcohol.

The invention may also provide a composition wherein the polyvinyl alcohol has a mean molecular weight of between 10 kDa and 400 kDa.

The invention may also provide a composition wherein the polyvinyl alcohol has a mean molecular weight of between 65 kDa and 90 kDa.

The invention may also provide a composition wherein the polyvinyl alcohol has a mean molecular weight of between 10 kDa and 35 kDa.

The invention may also provide a composition wherein the polymer microcapsules are in a second aqueous suspension.

The invention may also provide a composition wherein the second aqueous suspension also includes polyvinyl alcohol.

The invention may also provide a composition wherein the second aqueous suspension includes between 1% and 5% w/v of the polyvinyl alcohol.

The invention may also provide a composition wherein the second aqueous suspension includes between 2.5% and 5% w/v of the polyvinyl alcohol.

The invention may also provide a composition wherein the polyvinyl alcohol is in a higher concentration in the second aqueous solution than in the first aqueous solution.

The invention may also provide a composition wherein the polymer microcapsules are in a second aqueous suspension.

The invention may also provide a composition wherein the active bacteriophages are adsorbed on inorganic particles encapsulated in the polymer microcapsules.

The invention may also provide a composition wherein the bacteriophage related products are adsorbed on inorganic particles encapsulated in the polymer microcapsules.

The invention may also provide a composition wherein the inorganic particles include particles of at least one salt selected from the group consisting of $CaCO_3$, $Ca_3(PO_4)_2$, $MgCO_3$, and $Mg_3(PO_4)_2$.

The invention may also provide a composition wherein the inorganic particles have a mean size between 2 μm and 15 μm.

The invention may also provide a composition wherein the inorganic particles have a mean size between 2 μm and 4 μm.

The invention may also provide a composition wherein the polymer microcapsules have a mean size between 20 μm and 100 μm.

The invention may also provide a composition wherein the polymer microcapsules have a mean size between 20 μm and 50 μm.

The invention may also provide a composition wherein the polymer microcapsules have an upper limit size of 250 μm or less.

The invention may also provide a composition wherein the microcapsules are hollow and wherein a thickness of the polymer in the microcapsules is between 3% and 15% of the mean size.

The invention may also provide a composition wherein the polymer microcapsules have an upper limit size of 100 μm or less.

the at least one amino acid is chosen from naturally occurring amino acids and non-naturally occurring amino acid.

The invention may also provide a composition wherein the amino-acid based polymer is a poly (ester amide urea) comprising the following two blocks with random distribution thereof:

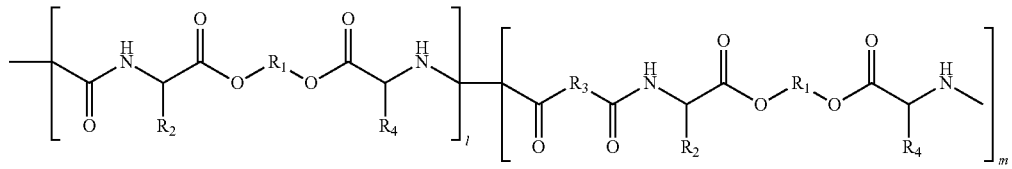

The invention may also provide a composition wherein the bacteriophage related products are selected from the group consisting of endolysins, lysostaphins, phage proteins, phage enzymatic formulations, and combinations thereof.

The invention may also provide a composition wherein the amino-acid based polymer is selected from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, (4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula:

HO—$R_1$—OH, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

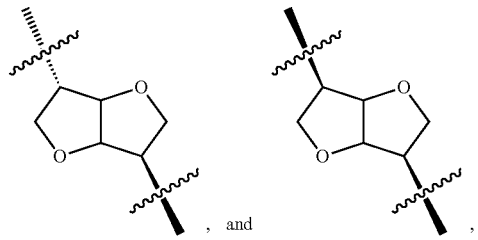

the at least one diacid is a compound of formula:

HO—(CO)—$R_3$—(CO)—OH, $R_3$ is $C_2$-$C_{12}$ alkylene, wherein the ratio of l:m ranges from 0.05:0.95 to 0.95:0.05, l+m=1, $R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes,

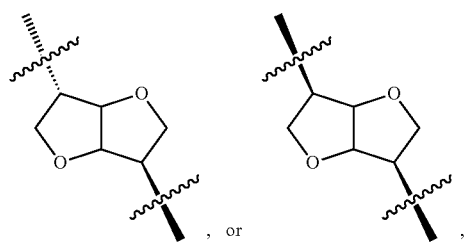

$R_3$ is $C_2$-$C_{12}$ alkylene, $R_2$ and $R_4$ are independently chosen from the side chains of L- and D-amino acids so that the carbon to which $R_2$ or $R_4$ is attached has L or D chirality.

The invention may also provide a composition wherein the ratio of l:m ranges from 0.25:0.75 to 0.75:0.25, l+m=1.

The invention may also provide a composition wherein $R_1$ is —$(CH_2)_6$—, $R_3$ is —$(CH_2)_8$— and both $R_2$ and $R_4$ are the side chain of L-leucine.

The invention may also provide a composition wherein the amino-acid based polymer has a polydispersity of 1.15 or less.

The invention may also provide a composition wherein the amino-acid based polymer has a molecular weight between 15 kDa and 30 kDa.

The invention may also provide a composition wherein the amino-acid based polymer is amorphous.

The invention may also provide a composition wherein the active bacteriophages include at least two different strains of bacteriophages.

The invention may also provide a composition wherein the at least two different strains of bacteriophages include strains of bacteriophages from more than one family.

The invention may also provide a composition wherein the composition is liquid form and has a viscosity small enough to allow pulverization through a nozzle.

The invention may also provide a composition wherein the composition is powder form.

The invention may also provide a composition wherein the composition is in liquid form, and the polymer microcapsules are suspended in a solution including a poloxamer.

The invention may also provide a composition wherein the poloxamer is poloxamer 407.

The invention may also provide a composition wherein the poloxamer is in a concentration of between 10 and 30 percent.

The invention may also provide a composition wherein the poloxamer has a mean molecular weight of between 9500 kDa and 15000 kDa.

The invention may also provide a composition wherein the composition is in gel form.

The invention may also provide a composition wherein the polymer microcapsules contain on average more than 4 active bacteriophages.

The invention may also provide a composition wherein the polymer microcapsules contain on average more than 100 active bacteriophages.

The invention may also provide a composition wherein the composition further includes active bacteriophages outside of the polymer microcapsules.

The invention may also provide a composition further including a drug selected from the set consisting of antibiotics, pain killer and hemostatic drug.

The invention may also provide a composition wherein the composition comprises active bacteriophages, and wherein the composition has a stability such that at least 10% of the active phages remain active after storage of the composition for one year at 4° C.

In another broad aspect, the invention provides a method for preparing a composition including polymer microcapsules in which at least one of active bacteriophages and bacteriophage related products are encapsulated in the polymer microcapsules, the method including: preparing a first aqueous phase; preparing a second aqueous phase including the at least one of active bacteriophages and bacteriophage related products suspended therein; preparing an hydrophobic phase including an amino-acid based polymer dissolved therein; emulsifying the first aqueous phase in the hydrophobic phase to prepare a primary emulsion; and emulsifying the primary emulsion in the second aqueous phase to prepare a secondary emulsion.

The invention may also provide a method wherein the primary emulsion includes the first aqueous phase and the hydrophobic phase in a ratio of from 1:2 to 1:20.

The invention may also provide a method wherein the primary emulsion includes the first aqueous phase and the hydrophobic phase in a ratio of about 1:10.

The invention may also provide a method wherein the secondary emulsion includes the primary emulsion and the second aqueous phase in a ratio of from 1:2 to 1:20.

The invention may also provide a method wherein the secondary emulsion includes the primary emulsion and the second aqueous phase in a ratio of from 1:2 to 1:5.

The invention may also provide a method further including evaporating the organic solvent.

The invention may also provide a method wherein the organic solvent is evaporated without transfer to a hardening tank.

The invention may also provide a method wherein the organic solvent includes at least one of dichloromethane (DCM), ethylacetate and chloroform.

The invention may also provide a method wherein the organic solvent includes dichloromethane (DCM).

The invention may also provide a method wherein emulsifying the first aqueous phase in the hydrophobic phase to prepare the primary emulsion includes stirring the first aqueous phase in the hydrophobic phase using an homogenizer operating a between 8000 RPM and 50000 RPM during preparation of the primary emulsion.

The invention may also provide a method wherein the homogenizer operates at 10000 RPM or less during preparation of the primary emulsion.

The invention may also provide a method wherein the homogenization of the primary emulsion lasts for 30 s or less.

The invention may also provide a method wherein emulsifying the hydrophobic phase in the second aqueous phase to prepare the secondary emulsion includes adding the primary emulsion dropwise to the second aqueous phase while stirring the second aqueous phase using a homogenizer operating a between 8000 RPM and 25000 RPM.

The invention may also provide a method wherein the homogenizer operates at 10000 RPM or less during preparation of the secondary emulsion.

The invention may also provide a method wherein homogenization lasts less than 30 s during preparation of the secondary emulsion.

The invention may also provide a method wherein homogenization lasts less than 10 s during preparation of the secondary emulsion.

The invention may also provide a method wherein emulsifying the hydrophobic phase in the second aqueous phase to prepare the secondary emulsion includes adding the primary emulsion to the second aqueous phase while stirring the second aqueous phase at between 100 and 1000 RPM.

The invention may also provide a method wherein the primary emulsion is added dropwise to the second aqueous phase.

The invention may also provide a method wherein stirring is performed using an object plunged in the second aqueous phase.

The invention may also provide a method wherein the object is a magnetic bar rotated by a magnetic stirrer.

The invention may also provide a method wherein stirring is performed at between 200 RPM and 600 RPM.

The invention may also provide a method wherein the hydrophobic phase includes from 5% to 20% w/v of polymer.

The invention may also provide a method wherein the hydrophobic phase includes about 13% w/v of polymer.

The invention may also provide a method further including dialysing the secondary emulsion.

The invention may also provide a method wherein the first aqueous phase includes Kolliphor P188.

The invention may also provide a method wherein the first aqueous phase includes polyvinyl alcohol.

The invention may also provide a method wherein the first aqueous phase includes between 1% and 5% w/v of the polyvinyl alcohol and the polyvinyl alcohol has a mean molecular weight of between 10 kDa and 100 kDa.

The invention may also provide a method wherein the second aqueous phase also includes polyvinyl alcohol.

The invention may also provide a method wherein the second aqueous phase includes between 1% and 5% w/v of the polyvinyl alcohol and the polyvinyl alcohol has a mean molecular weight of between 10 kDa and 100 kDa.

The invention may also provide a method wherein the bacteriophage related products are selected from the group consisting of endolysins, lysostaphins, phage proteins, phage enzymatic formulations, and combinations thereof.

The invention may also provide a method wherein the amino-acid based polymer is any of the polymers selected from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, (4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula: HO—$R_1$—OH, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

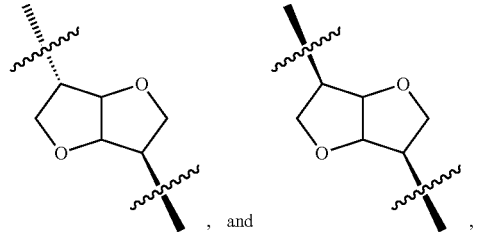

, and the at least one diacid is a compound of formula: HO—(CO)—$R_3$—(CO)—OH, $R_3$ is $C_2$-$C_{12}$ alkylene, the at least one amino acid is chosen from naturally occurring amino acids and non-naturally occurring amino acid.

The invention may also provide a method wherein amino-acid based polymer is a poly (ester amide urea) comprising the following two blocks with random distribution thereof:

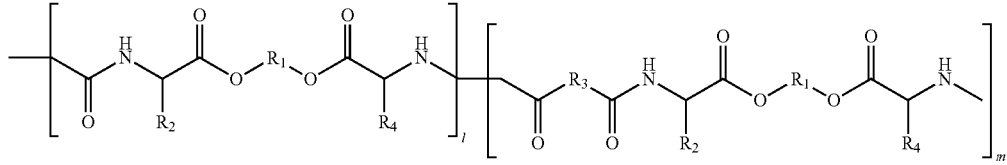

wherein the ratio of l:m ranges from 0.05:0.95 to 0.95:0.05, l+m=1, $R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes,

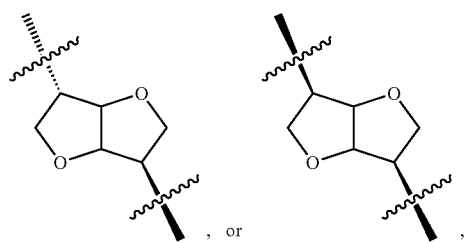

, or $R_3$ is $C_2$-$C_{12}$ alkylene, $R_2$ and $R_4$ are independently chosen from the side chains of L- and D-amino acids so that the carbon to which $R_2$ or $R_4$ is attached has L or D chirality.

The invention may also provide a method wherein the ratio of l:m ranges from 0.25:0.75 to 0.75:0.25, l+m=1.

The invention may also provide a method wherein $R_1$ is —$(CH_2)_6$—, $R_3$ is —$(CH_2)_8$— and both $R_2$ and $R_4$ are the side chain of L-leucine.

The invention may also provide a method wherein the amino-acid based polymer has a molecular weight between 15 kDa and 30 kDa.

The invention may also provide a method further including dissolving polyvinyl alcohol in the secondary emulsion after formation of the secondary emulsion.

The invention may also provide a method further including dissolving a gelling agent in the secondary emulsion.

The invention may also provide a method wherein the gelling agent is poloxamer 407.

The invention may also provide a method wherein the gelling agent is a poloxamer having a mean molecular weight of between 9500 kDa and 15000 kDa.

The invention may also provide a method wherein the second aqueous phase includes the active bacteriophages at between $10^7$ and $10^{14}$ PFU/mL.

Advantageously, in some embodiments, the present invention allows formation of encapsulating polymer microcapsules that are large enough (for example several tens of microns or more) to contain a useful quantity of bacteriophages. In addition, amino acid based biodegradable polymers (AABBPs) for medical applications are superior to the currently commercialized polyesters. They possess vast availability of variable building blocks, which makes it possible to synthesize various copolymers containing fragments of different classes, allowing to design biodegradable polymeric biomaterials with a widely tunable physical-chemical, biochemical and mechanical properties—from viscous-flow and elastic to high-strength materials.

The polymers chosen in the present patent application have NH—CO bonds that provide a high affinity with tissues. In some embodiments, after biodegradation the AABBPs release weaker acidic products in much lower quantities as compared with poly-α-hydroxy acids, thus increasing their biocompatibility with mammalian/human cells. For example, one of the building blocks of PEAU, PEAs release neutral (zwitterionic) amino acids and diols, and relatively week fatty diacids (e.g. adipic acid with pKa 4.43 and 5.41) after its final hydrolysis. The other building block of PEAU, PEU, releases normal metabolites such as $CO_2$ and amino acids, and neutral and readily metabolized diols, following degradation.

Another advantage for microencapsulation and smooth biodegradation is that these AABBPs are, in some embodiments, amorphous, or have a semi-crystalline structure that has a unique property of becoming amorphous and retaining its structure after melting/cooling cycle.

AABBPs possess typically much higher shelf life compared to poly(lactic/glycolic acid) polymers because as polycondensation type polymers they do not subject depolymerization in storage.

For orthopedic and medical device applications, the biodegradable polymer obtained on the basis of the PEU composed of L-phenylalanine and 1,6-hexanediol, has a Young's modulus up to 6.1±1.1 GPa. These are the first degradable polymeric constructs with moduli in the range of 6.0 GPa, which is substantially higher than the moduli of other, commercially available and widely used polyesters including tyrosine derived polycarbonates (≈1-2 GPa), poly (L-lactic acid), PLLA (≈3-3.5 GPa), and poly(propylene fumarate) (2.2 GPa) used in numerous regenerative medicine and orthopedic applications. The obtained mechanical and biochemical data show that the new PEU materials may be apt to provide structural support and facilitate new tissue regeneration strategies in load bearing applications.

Another significant limitation of polyesters, such as polycaprolactone and PLLA, is that they degrade very slowly. It can take years for these materials to degrade and resorb fully, and the associated acidification that results often leads to inflammation. Contrariwise, the biodegradation of PEUs does not typically cause a local acidic environment causing inflammation to build up. During melting assays, the Tg of PEU remained the same with no melting peak observed, indicating that no crystallinity was present. This provides relatively quick and complete biodegradation in contrast to e.g. PLLA in which the high initial crystallinity form large amounts of tiny and rough highly resistant particles when the amorphous phase was degraded. Such particles are now known as very inflammatory and thus well explain the late dramatic inflammatory response observed in many studies.

Advantageously, PVA had been found to be an excellent surfactant for preparing microcapsules by W/O/W double emulsion method. PVAs of various molecular weights (31,000 and 84,000-89,000 Da) were used, and very good microcapsules (in terms of sized and size distribution) were fabricated, but other molecular weights are also usable. High-molecular-weight PVA forms microcapsules of desired size, and allows for the formation of an elastic films after evaporation of water, thus, it is of high interest for preparing various types of bacteriophage containing film-like wound dressings. Adherence of the microcapsules suspension to the wound site can be optimized by the addion of a high-molecular-weight PVA (84,000-89,000 Da) to the microcapsule suspension, which will allow for the formation of an elastic film after the evaporation of water content. Water-based spray dressings are promising since organic solvents like chloroform and dichloromethane are prohibited for medical uses, and although ethanol has been approved for medical applications, it inactivates bacteriophages. Advantages of using PVA, includes the property of PVA so slowly dissolve in liquid environments, such as in the wound exudate, bodily fluids, etc., allowing for a slow release of the entrapped bacteriophages.

PVA can also be used for preparing simple and inexpensive spray dressing. Addition of PVA to bacteriophages in solution allows for the formation of a viscous solution that can be applied to a surface (wounds, plants, medical devices, implants, etc., forming an elastic film after evaporation of its water content, on the said surface. Again, PVA so slowly dissolve in liquid environments, such as in the wound exudate, bodily fluids, etc., allowing for a slow release of the entrapped bacteriophages.

Similarly, Poloxamer can be used for preparing such dressings. Poloxamer are modulable nonionic triblock copolymers: the central hydrophobic chain of polyoxypropylene and the two hydrophilic side chains of polyoxyethylene are customizable in terms of length. Poloxamer sol-gel properties are of high interest: solutions of concentrated poloxamer are liquid at low temperatures and undergo sol-gel transition at higher temperatures. This process is reversible. For example Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, can be used. In particular, thermoreversible hydrogels are in situ forming gels that undergo sol-gel transition with an increase of temperature. Examples of such poloxamers are P188, P237, P338, and P407.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
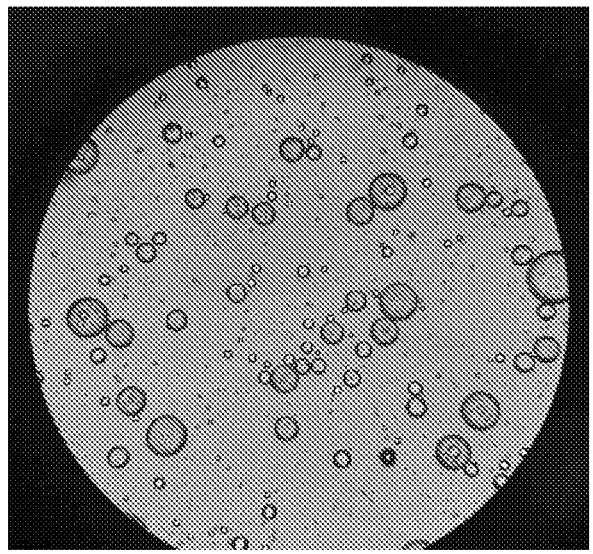
FIG. 1, in an optical microscope image, illustrates Formulation 9, prepared according to example 1, with microcapsules containing *Staphylococcus aureus* phage J1P1

The examples below use a polymer referred to as PEAU. This polymer is a poly (ester amide urea) comprising the following two blocks with random distribution thereof:

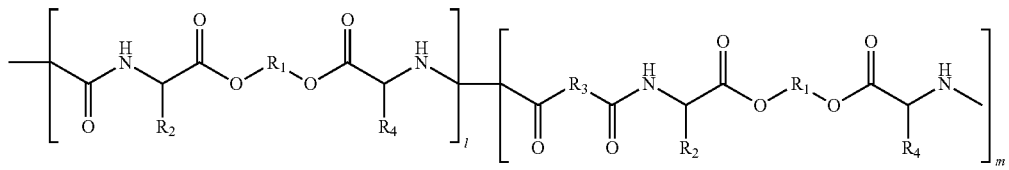

wherein
the ratio of l:m ranges from 0.05:0.95 to 0.95:0.05, l+m=1, $R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes,

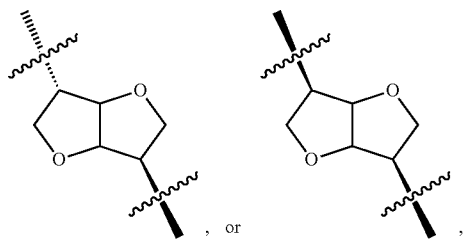

$R_3$ is $C_2$-$C_{12}$ alkylene, $R_2$ and $R_4$ are independently chosen from the side chains of L- and D-amino acids so that the carbon to which $R_2$ or $R_4$ is attached has L or D chirality.

The more specific polymer referred to in the examples is the polymer wherein $R_1$ is —$(CH_2)_6$—, $R_3$ is —$(CH_2)_8$— and both $R_2$ and $R_4$ are the side chain of L-leucine. These polymers are referred to hereinbelow in abbreviated form as $(8L6)_l$-$(1L6)_m$.

Summary of Examples 1 to 3

In example 1, the proposed method uses a high-speed homogenization of a 13% PEAU solution in dichloromethane (DCM) with a 1% 67 kDa polyvinyl alcohol (PVA) solution, dropped in a 2% PVA bacteriophages solution. After overnight evaporation of the solvent, the formulation in example 1 is ready to use as is or for further formulations (see examples 2 and 3). A portion of the bacteriophages remains in the external liquid, that will act as a short-time release (direct kill), and microcapsules contain the remainder of the bacteriophages, and will allow a further long-term release due to biodegradation. The formulation in example 2 is fabricated by adding 3% w/v of 67 kDa PVA to F9, the formulation of Example 1 (final 5% w/v PVA). This formulation is to be used, for example, as a film because high molecular weight PVA forms elastic film after evaporation of water, which is appropriated for sprays, among other applications.

The 3$^{rd}$ example is a gel formulation composed of the composition of example 1 supplemented by 25% w/v of Poloxamer P407. (This concentration can be modified at will to get the appropriate viscosity). Poloxamer P407 possess inverse thermosensitivity, which means it is liquid at low temperatures (2-4° C.) and will gel at high temperature (higher than 20° C.) so is useful for many applications, for example for the treatment of 3$^{rd}$-degree burns.

Example 1: Preparation of Large Microcapsules Containing Bacteriophage

The following protocol was performed in this example:
1. Clean and sterilize all beakers, erlenmeyers, stoppers, funnels and vessels.
2. Prepare the stock solution of Polyvinyl Alcohol (PVA) (1.0% w/v) in water for the primary emulsion:
a) put 100.0 mg (0.1 g) of PVA in a lab. flacon (20.0 mL capacity) or a small beaker (max 50 mL)
b) add 10.0 mL of water
c) put a magnetic stirring bar in the flacon/beaker
d) place the flacon on a magnetic stirrer
e) switch the stirrer, select stirring rate 100-200 rpm (avoid splashing)
f) stir until complete dissolution of PVA (overnight)
g) take the solution in a sterile syringe and pour through 0.22 um filter in a sterile lab flacon under the laminar hood
h) place and store in a refrigerator (if not use in the same day).
3. Prepare the PVA solution (2.0% w/v) in the liquid phages (or TMN buffer depending on the task (TMN buffer can be used as a control)) for the secondary emulsion:
a) put 400.0 mg (0.4 g) of PVA in a sterile erlenmeyer, capacity max. 200.0 mL under laminar hood
b) put a sterile magnetic stirring bar in the Erlenmeyer under laminar hood
c) add 20.0 mL of the liquid phage (or TMN buffer) under laminar hood
d) seal Erlenmeyer with a sterile foam under the laminar hood
e) put the beaker on a magnetic stirrer
f) switch the stirrer, select stirring rate 100-200 rpm (avoid splashing)
g) stir until complete dissolution of PVA (overnight)
h) store in a fridge (if not used the same day)
i) take the solution in a sterile syringe and pour through 0.22 um filter in a sterile glass beaker (cap. 50 mL) under the laminar hood
j) cover with a sterile glass watch under the laminar hood
4. Prepare the polymer solution (13.0% w/v) for the primary emulsion:
a) put 1.04 g of the PEAU $(8L6)_{0.6}$-$(1L6)_{0.40}$ in a small Erlenmeyer flask (max 50 mL)
b) add 8.0 mL of DCM to the polymer in the flask
c) put a magnetic stirring bar in the flask
d) seal the flask with stopper wrapped in Teflon tape
e) put the sealed small Erlenmeyer flask on the magnetic stirrer
f) switch the magnetic stirrer on, select stirring rate 100-200 rpm (avoid splashing) and stir until complete dissolution of the polymer
g) place it in a refrigerator (if not use in the same day).

5. Assemble the following set-up under the chemical hood: A small dropping funnel with Teflon stopcock, capacity 20.0, max. 50.0 mL fixed to a lab stand, above a magnetic stirrer.
6. Prepare the primary emulsion:
a) open (remove stopper) the Erlenmeyer flask with the polymer solution
b) move the polymer solution (8 mL) to a sterile Lab flacon with stopper, capacity 20.0 mL, d=2.0-2.5 cm, under the chemical hood
c) take 0.8 mL from the PVA's stock solution (1%)
d) quickly add this 0.8 mL to 8.0 mL the polymer solution
e) put a dispersing element of a high speed homogenizer in the solution
f) switch the homogenizer, select the rate 10,000 rpm
g) homogenize for 15 sec.
h) remove the high speed homogenizer
i) seal the flacon with the cap
j) immediately use for preparing the secondary emulsion
7. Prepare the secondary emulsion (under chemical hood):
a) remove the primary emulsion, from the flacon to the dropping funnel
b) seal the dropping funnel
c) put the glass beaker with PVA solution (2.0% w/v) in the liquid phages (or TMN buffer), on a magnetic stirrer
d) it is preferable to fix the beaker to the lab stand
e) switch the magnetic stirrer and select stirring rate 400 rpm.
f) remove the covering (watch glass) from the beaker
g) add dropwise (ca. 1-2 drops per sec.) the primary emulsion from the dropping funnel to the beaker containing PVA's solution (2%) in the liquid phage (or TMN buffer)
h) cover the beaker with the watch glass again (to prevent dust and bacterial invasion)
i) stir at 400 rpm for 18 h until complete evaporation of DCM
j) stop the stirrer
k) go under the laminar hood to remove the covering (watch glass) from the beaker
l) move the obtained MSs suspension to a sterile lab flacon with a stopper of capacity max. 100 mL, seal the flacon with the stopper and store the suspension in a refrigerator
m) use the obtained suspension for subsequent analysis FIG. 1 is a microscopy image of a typical composition resulting from these manipulations. The microcapsules are clearly seen. They have a substantially spherical shape with a hollow interior in which a bacteriophage suspension is encapsulated. Scanning electron microscope (SEM) images were also acquired as follows. A drop of each wet sample of microcapsules (obtained as per the method described above) was placed on a clean aluminum stub and dried under vacuum. The SEM (scanning electron microscope) observations were performed on a JEOL JSM-7600F equipped with a field emission gun (FEG) operated at 1 kV. All the images were acquired using the lower secondary electron detector (LEI). The image analysis was performed by measuring by hand the diameter of more than 300 spheres on calibrated images using the ImageJ software (https://imagej.nih.gov/ij/).

Figure 2:
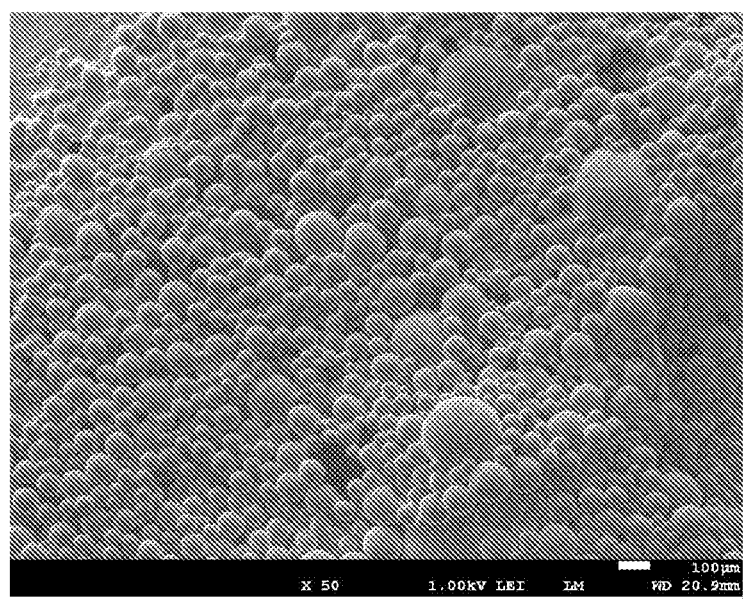
FIG. 2, in an FEG-SEM image, illustrates amino-acid based microcapsules containing *Staphylococcus* phage BP39 prepared according to example 1.
Figure 3:
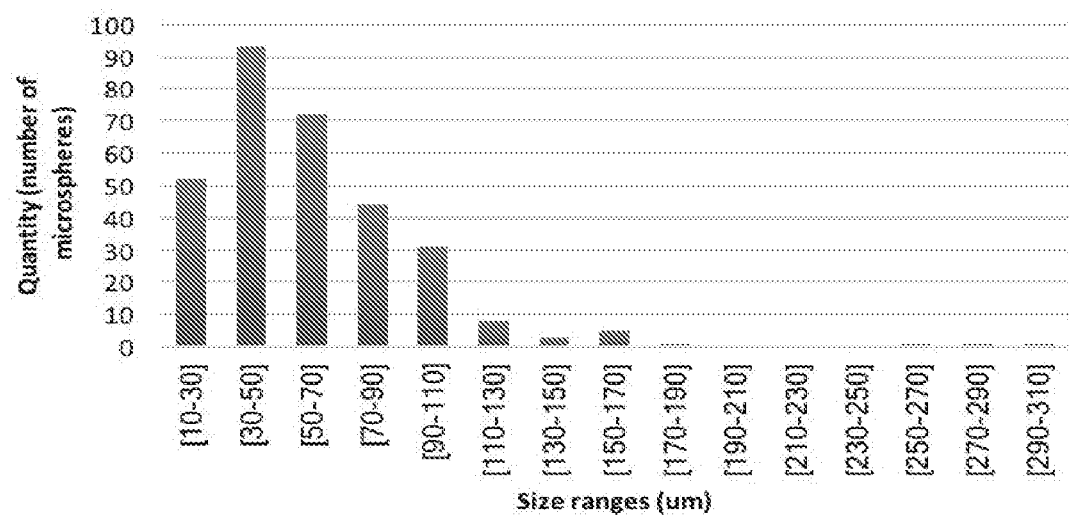
FIG. 3, in a bar chart, illustrates the size distribution of microspheres containing *S. aureus* phage BP39 prepared according to example 1.

An example of the resulting images is seen in FIG. 2 and the size distribution of the microcapsules (ie the polymer phase) is shown in FIG. 3. The size distribution characteristics for the composition including the BP39 phages were: minimum diameter: 11.15 μm; maximum diameter: 304.77 μm; mean diameter: 60.72 μm and std deviation of diameter: 37.90 μm.

Figure 4:
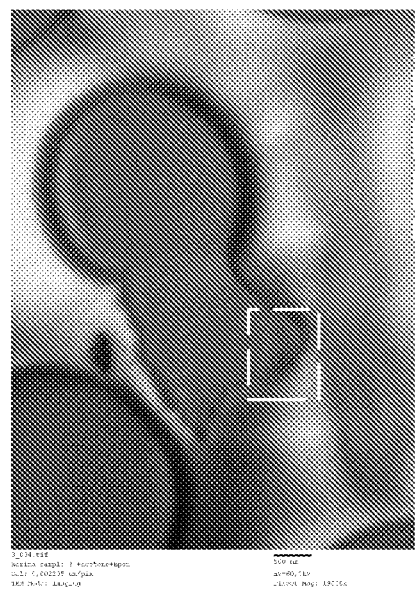
FIG. 4, in a TEM image, illustrates bursting microtomied microspheres containing phages prepared according to example 1.
Figure 5:
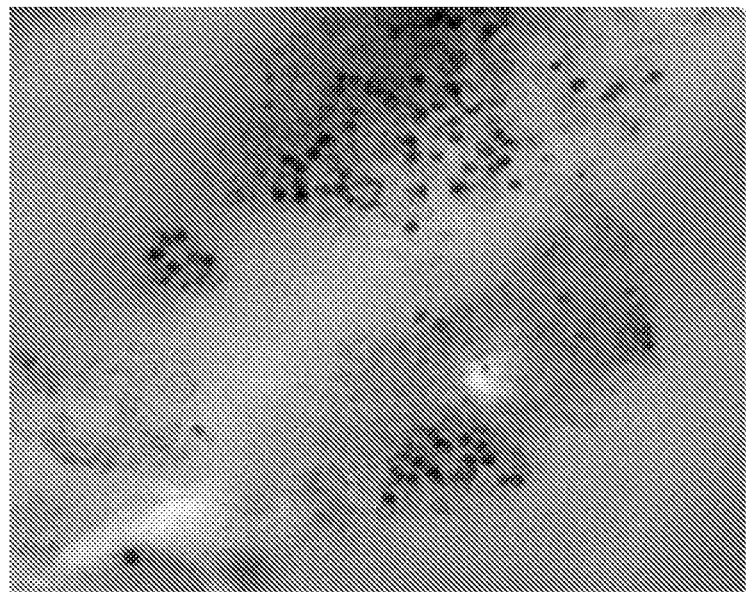
FIG. 5, in a TEM image, illustrates the portion of FIG. 4 found in the white dashed box.

FIGS. 4 and 5 illustrate TEM images of the microcapsules (formulation 9, ie the formulation of example 1, also referred herein as F9), which confirms the presence of phages inside the microcapsules in F9. More specifically, detection of phages inside newly synthesized microcapsules was performed by fixing microcapsules by immersion with gluteraldehyde and dehydration with ethanol at 4° C. Tissue samples were embedded in Epon resin according to routine techniques and thin sections (100 nm) of tissues were processed by microtoming and mounted on Parlodion-carbon coated grids, counterstained with uranyl acetate, and examined under conventional transmission electron microscope at 80 kV. FIG. 5 is en enlargement of the dotted box of FIG. 4.

Volatile organic compounds presence was evaluated as follows. Approximatively 500 mg of standard or samples (F9) were resolubilized in 9 mL of water containing 7 g of ammonium sulphate and 200 μL of internal standard, then heated for 1 hour at 120° C. Measurement was taken with a GC-MS from Agilent Technologies. 100 μL of gas was injected with a split ratio of 1:10. The temperature was set as following: 35° C. for 5 min, 10° C./min to 90° C., 50° C./min to 250° C. Calibration curves were prepared using DCM, cyclohexane and toluene. Internal standards used were cyclohexane-d12 and toluene-d18, cyclohexane-d12 being used to correct both the signal of DCM and cyclohexane. Results are summarized in the following Table 1:

TABLE 1

| Residual solvents concentration in F9 (ppm) | | | |
| --- | --- | --- | --- |
| | DCM | Cyclohexane | Toluene |
| USP limits | 600 | 3880 | 890 |
| F9 (TMN) | <60 | <388 | <89 |
| F9 (BP39) | <60 | <388 | <89 |

This formulation thus does not contain any significant amounts of residual organic solvent and follows ISO requirements for medical devices. The values are below the detection of the method.

Figure 6:
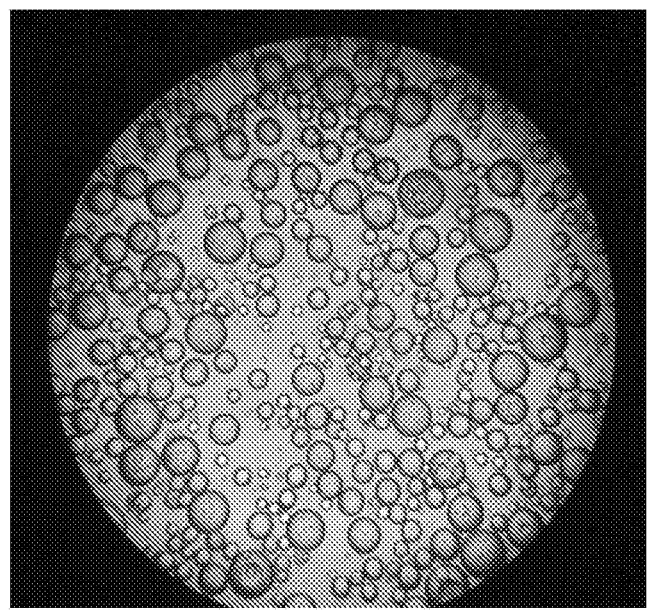
FIG. 6, in a microscope image, illustrates formulation 9 of FIG. 1 42 days after preparation (008 J1P1, 42 days old).

Stability was evaluated as follows. Samples were centrifugated slightly and supernatant was pipetted. After titration, microcapsules were resuspended. The formulations were stable for over 30 days at room temperature and 4° C., as illustrated in FIG. 6 illustrates a typical as seen through a microscope 42 days after preparation. The microcapsules' appearance is similar to the appearance just after preparation illustrated in FIG. 1.

Phages titer inside microcapsules (MCs) were performed as follows.

Preliminary assay 1: 500 μL of F9 lot #011BP39 were taken and centrifuged 3 min at 2000 RPM. Supernatant was removed (sample 1)—note that the weight of the MCs was 0.05 g- and MCs were washed with 500 μL of TMN, and centrifuged 3 min at 2000 RPM. Supernatant (sample 2) was removed and the wash was repeated (sample 2◊7)—note that due the losses during the washes the weight of the MCs was then 0.04 g. Finally, 500 µL of DCM was added to break MCs. Approx. 17.5 µL of TMN solution was recovered from the MCs (sample D). Results are shown in Table 2.

TABLE 2 inside titration of phages in F9 lot #011BP39 in preliminary assay 1

| | Sample | | | |
|---|---|---|---|---|
| | 1 | 2 | 3 | 4 |
| PFU/mL | 7.50E+09 | 1.70E+09 | 1.90E+08 | 4.50E+07 |
| | Sample | | | |
| | 5 | 6 | 7 | D |
| PFU/mL | 1.00E+07 | 4.60E+06 | 2.50E+06 | 1.30E+08 |

The results for D (dissolved microcapsules) is the sum of the result for the last wash plus the phages liberated by the microcapsules. So the MCs liberated $1.28*10^8$ PFU/mL in the 17.5 µL eg $2.23*10^6$ PFU, eg $5.58*10^7$ PFU/g of MCs.

Preliminary assay 2: 1 mL of F9 lot #011BP39 were taken and centrifuged 3 min at 2000 RPM. Supernatant was removed (sample 1)—note that the weight of the MCs was 0.1 g- and MCs were washed with 1 mL of TMN, and centrifuged 2 min at 2000 RPM. Supernatant (sample 2) was removed and the wash was repeated (sample 2 ◊ 11). Finally, 1.5 mL of DCM and 100 µL of TMN were added to break MCs and dissolve phages. Less than the 100 µL of TMN solution were recovered from the MCs (sample D). In this experiment, it is clear that MCs broke during the washing process, regarding that the titers in the successive washed are not decreasing. Similarly to the previous assay an the amount of encapsulated bacteriophages where of $4.8*10^7$ PFU/g of MCs. Results are found in Table 3.

TABLE 3 inside titration of phages in F9 lot #011BP39 in preliminary assay 2

| | Sample | | | | | |
|---|---|---|---|---|---|---|
| | 1 | 2 | 3 | 4 | 5 | 6 |
| PFU/mL | 7.40E+09 | 1.10E+09 | 1.70E+08 | 3.30E+07 | 2.80E+07 | 5.00E+06 |
| | Sample | | | | | |
| | 7 | 8 | 9 | 10 | 11 | D |
| PFU/mL | 3.50E+06 | 1.60E+06 | 1.00E+06 | 4.50E+05 | 4.10E+05 | 4.80E+07 |

Preliminary assay 3: 500 µL of F9 lot #011BP39 were taken and centrifuged 3 min at 2000 RPM. Supernatant was removed (sample 1)—note that the weight of the MCs was 0.05 g- and MCs were washed with 500 µL of TMN, and centrifuged 2 min at 2000 RPM. Supernatant (sample 2) was removed and the wash was repeated (sample 2 ◊ 3). MCs were kept in 2$^{nd}$ wash (sample 3) and finally, 1 mL of DCM was added to break MCs and dissolve phages. TMN solution was recovered (sample 3*). Results from this assay are found in Table 4.

TABLE 4

Inside titration of phages in F9 #011_BP39 (preliminary test 3)

| | Sample | | | |
|---|---|---|---|---|
| | 1 | 2 | 3 | 3* |
| PFU/mL | 4.70E+09 | 5.00E+08 | 1.20E+08 | 2.80E+08 |

This method avoids the break of the MCs during the washes. Encapsulated phage concentrations are of $1.6*10^9$ PFU/g of MCs. Moreover, a film of polymer forms at the interface between DCM and TMN. One drop of this interface was put on the titration plate (under the SaA29 writing), and shows a clear lysis. This means a lot of phages are trapped in at the interface, that still contains MCs, which was confirmed through visual inspection.

Preliminary assay 4: 500 µL of F9 lot #011BP39 were taken and centrifuged 3 min at 2000 RPM. Supernatant was removed (sample 1)—note that the weight of the MCs was 0.04 g- and MCs were washed with 500 µL of sterile water, and centrifuged 3 min at 2000 RPM. Supernatant (sample 2) was removed and the wash was repeated (sample 2 ◊ 6). Last supernatant was removed (sample 6) and 1 mL of DCM was added to break MCs and dissolve phages. After 10 min, 100 µL of sample 6 was added to the mix, vortexed again and centrifuged 5 min at 2000 RPM to separate phases. Sample F1 was then taken in the aqueous phase. After another 5 min and vortexing, sample B was taken in a bubble of aqueous phase. Sample F3 was taken after 30 min (after addition of DCM). The polymeric interphase was not pipetted because it was too small. This gives $3.58*10^7$ PFU/g of MCs. Quantitative results are found in Table 5.

TABLE 5

Inside titration of phages in F9 #011_BP39 (preliminary test 4)

| | Sample | | | |
|---|---|---|---|---|
| | 6 | F1 | B | F3 |
| PFU/mL | 3.60E+06 | 1.20E+07 | 1.70E+07 | 1.40E+07 |

Final titration: 500 µL of F9 were taken and centrifuged 3 min at 2000 RPM. Supernatant was removed (sample 1) and MCs were washed with 500 µL of sterile water, and centrifuged 3 min at 2000 RPM. Supernatant (sample 2) was removed and the wash was repeated (sample 2◊6). Last supernatant was removed (sample 6) and 1 mL of DCM was added to break MCs and dissolve phages. After 10 min, 100 µL of sample 6 was added to the mix, vortexed again and centrifuged 5 min at 2000 RPM to separate phases. Sample F was then taken in the aqueous phase. Quantitative results are found in Table 6.

TABLE 6

Inside phages titers in formulations 9

| F9 lot # | Date of production | Age of the sample at the time of analysis (days) | Phages | Phages titer before encapsulation (PFU/mL) | Inside MCs phages titer (PFU/g of wet MCs) | Inside MCs phages titer (PFU/mL of F9) |
| --- | --- | --- | --- | --- | --- | --- |
| 003 | 6 Apr. 2016 | 63 | BP39 | $1.8 \cdot 10^{11}$ | $2.17 \cdot 10^7$ | $2.6 \cdot 10^6$ |
| 008 | 27 Apr. 2016 | 42 | J1P1 | $6.5 \cdot 10^9$ | $4.91 \cdot 10^6$ | $5.89 \cdot 10^5$ |
| 009 | 27 Apr. 2016 | 42 | J21P1 | $4.6 \cdot 10^8$ | $6.5 \cdot 10^4$ | $7.8 \cdot 10^3$ |
| 010 | 27 Apr. 2016 | 42 | J1P3 | $8.5 \cdot 10^8$ | $5.37 \cdot 10^5$ | $6.44 \cdot 10^4$ |
| 011 | 27 Apr. 2016 | 42 | BP39 | $3.6 \cdot 10^{10}$ | $3.58 \cdot 10^7$ | $3.58 \cdot 10^6$ |
| 013 | 16 May 2016 | 23 | J1P1 | $6.5 \cdot 10^9$ | $1.52 \cdot 10^6$ | $1.52 \cdot 10^5$ |
| 014 | 16 May 2016 | 23 | J21P1 | $4.6 \cdot 10^8$ | $1.49 \cdot 10^6$ | $8.92 \cdot 10^4$ |
| 015 | 16 May 2016 | 23 | J1P3 | $6.5 \cdot 10^9$ | $1.23 \cdot 10^6$ | $1.23 \cdot 10^5$ |
| 016 | 16 May 2016 | 23 | BP39 | $3.6 \cdot 10^{10}$ | $2.95 \cdot 10^6$ | $2.36 \cdot 10^5$ |

Phages inside MCs and the phages trapped in the polymer or at the surface are titrated by this method. The results seem to indicate that phages are also stable inside the MCs, and that the higher the initial titer is, the higher the encapsulated titer is. Prolonged storage experiments showed that storage at 4° C. or room temperature is also possible for at least one year while preserving phage activity.

Example 2

This example aims at preparing a suspension with the bacteriophage loaded microcapsules (MCs) containing higher concentration (5% w/v) of PVA (Formulation #10, also F10 hereinbelow). The following protocol was performed in this example:
1. Clean and sterilize all beakers, funnels, magnetic stirring bar, and vessels for storing the product.
2. Prepare the phage loaded suspension according to the Protocol given in example 1.
3. When all DCM has been evaporated in Formulation 9, take either the beaker with the glass watch or the flacons in which the MCs are stored under the laminar hood.
4. Put a sterile stirring bar in a sterile flacon with cap.
5. Outside the laminar hood, weigh 600.0 mg (0.6 g) of solid PVA on a sterile glass watch with a spatula previously plunged into alcohol
7. Under laminar hood, transfer the powder in the sterile flacon with a spatula previously plunged into alcohol.
8. Add 20 mL of resuspended (vortexed) Formulation 9 in the flacon with a sterile pipet of 20 mL.
9. Put the sterile cap on the flacon.
10. Put the flacon on the magnetic stirrer in the chemical hood for 24 h until complete dissolution of the PVA.
11. Stop the stirrer and store Formulation 10 at 4° C.
12. Use the obtained Formulation 10 for subsequent tasks.
FIGS. 6 and 7 illustrate typical results preparations prepared according to the protocol of this example shortly after preparation (FIG. 6) and after 23 days (FIG. 7).

Stability was quantified as follows. Samples were centrifuged slightly and supernatant was pipetted. After titration, microcapsules were resuspended. The MCs were stable and the phages remained active both at 4° C. and at room temperature for at least one year.

Example 3

This example concerns preparation of the suspension with the bacteriophages loaded microcapsules (MCs) containing higher concentration (25% w/v) of Poloxamer P 407 (Formulation #11, also F11 below). Poloxamer P 407 is soluble in water at low temperatures (3-5° C.). The formulation will be gelled upon heating up to 20-25° C. or higher temperatures (e.g. physiological temperature 36-37° C.). The following protocol was performed:
1. Clean and sterilize all beakers, funnels, magnetic stirring bar, and vessels for storing the product
2. Prepare the phage loaded suspension according to the Protocol given in example 1.
3. When all DCM has been evaporated in Formulation 9, take either the beaker with the glass watch or the flacons in which the MCs are stored under the laminar hood.
4. Put a sterile stirring bar in a sterile flacon with cap.
5. Outside the laminar hood, weigh 5.0 g of solid Poloxamer P 407 on a sterile glass watch with a spatula previously plunged into alcohol.
6. Under laminar hood, transfer the powder in the sterile flacon with a spatula previously plunged into alcohol.
7. Add 20 mL of resuspended (vortexed) Formulation 9 in the flacon with a sterile pipet of 20 mL.
8. Put the sterile cap on the flacon.
9. Put the flacon on the magnetic stirrer in the fridge for 24 h until complete dissolution of the Poloxamer.
10. Stop the stirrer and store Formulation 11 at 4° C.
11. Use the obtained Formulation-11 for subsequent tasks.
This preparation's stability was assessed as above. It was stable for up to more than a one year at 4° C. Since this preparation becomes a gel at higher temperatures, stability at room temperature was not assessed.
Microencapsulated formulations of examples 1, 2 and 3 (liquid spray, spray-patch, and spray-gel) containing cocktails of phages are stable and maintain their activity at 4° C. and room temperature. Stability of the formulation and activity of the encapsulated phages are still stable at room temperature, we are at time point 220 days for the liquid spray, 284 days for the Spray-Patch, and 288 days for the spray-gel. More detailed results are presented in Table 7 below

TABLE 7

Stability of the preparations of examples 1 to 3

| Formulation | Individual Cocktail | Stability and activity of encapsulated formulations | | |
|---|---|---|---|---|
| | | 4° C. | 22° C. | 37° C. |
| Liquid spray (Formulation 9 of example 1) | Individual | Ongoing, over 1 year | 113-over 277 days | 5-30 days |
| | Cocktail | Ongoing, 220 days | Ongoing, 220 days | 20 days |
| Spray-patch (Formulation 10, 5% PVA of example 2) | Individual | Ongoing, over 1 year | 84-250 days | 15-60 days |
| | Cocktail | Ongoing, 284 days | Ongoing, 284 days | 15 days |
| Spray-gel (Formulation 11, Poloxamer of example 3) | Individual | Ongoing, over 1 year | Over 230 days | 15-58 days |
| | Cocktail | Ongoing, 288 days | Ongoing, 288 days | 15 days |

Example 4: Rough Polymeric Microcapsules

In another embodiment, the bacteriophages are adsorbed by inorganic salts—calcium carbonate ($CaCO_3$) and calcium phosphate ($Ca_3(PO_4)_2$), prior to formation of microcapsules.

We have repeatedly studied the adsorption of bacteriophages by the water insoluble salts of calcium—$CaCO_3$ and $Ca_3(PO_4)_2$. In these experiment new phages preparations TG-1 and TG-2 were used. The data listed in Table 8 confirm that the bacteriophages are adsorbed by these salts.

TABLE 8

Insoluble calcium salts containing adsorbed bacteriophages

| | | PFU* | | |
|---|---|---|---|---|
| | Bacteriophages | Phages TG1 | $CaCO_3$* | Phages TG2 | $Ca_3(PO_4)_2$* |
| 1 | Staphylococcus | $10^8$ | $10^5$ | $10^9$ | $10^7$ |
| 2 | E. coli | $10^9$ | $10^6$ | $10^9$ | $10^8$ |
| 3 | Streptococcus | $10^8$ | $10^6$ | $10^8$ | $10^7$ |
| 4 | Ps. aeruginosa | $10^8$ | $10^6$ | $10^9$ | $10^7$ |
| 5 | Proteus | $10^8$ | $10^6$ | $10^8$ | $10^8$ |

*PFU of the bacteriophages desorbed from the salts.

These salts can be great products for the application in agriculture to treat plants. Calcium carbonate is used for decreasing acidity of the soil, and calcium carbonate is used as a fertilizer. Hence, the salts with absorbed bacteriophages can fulfill (at least) double function—to kill parasitic bacteria and to refine the soil. The salts are of a high interest for the application in livestock as well, e.g. to treat animals from pathogenic form of E. coli (carbonate salt will protect the bacteriophages from the inactivation by the acidic medium of stomach). The salts are also highly promising for medical applications as well in bone surgery, dentistry, etc.

These salts can be applied as either dry powders or in combination with PVA and Poloxamer. With these polymers (industrial products) the pulverizable composite can be obtained. The vehicles such as PVA and Poloxamer will allow to better fixing the salts' particles at various surfaces.

In some embodiments, the salts are incorporated in grindable polymeric microparticles forming the microcapsules. For example the polymer is a low molecular weight (LMW) polymer based on 1L6. The protocol for preparing bacteriophage loaded rough polymeric microparticles is given below.

In an exemplary procedure, 2.0 g of LMW-1L6 was dissolved in 20.0 mL of DCM at room temperature and 2.0 g of dry calcium carbonate ($CaCO_3$) with mean particle size 6.2 µm was used for this purpose) containing absorbed bacteriophages and was thoroughly homogenized for 15 min at 22,000 rpm using a high speed-homogenizer, and cast onto a Teflon plate, DCM was evaporated at room temperature and atmospheric pressure until dried, and the obtained brittle film was subsequently dried under vacuum at 30° C. for 20 hours. The film was removed from the Teflon backing, grinded mechanically in a porcelain pounder and sieved through 90 µm mesh-size sieve. The results of particles size and size distribution determination following grinding and sieving through 90 µm mesh-size sieve are given in Table 9. The particles mean size right after grinding was 65.28 µm and upper limit size was 175.47 µm which is acceptable for preparing suspension used for purpose of spraying surfaces, such as wounds, using a spraying apparatus with the a nozzle diameter of 250-300 µm. Mean size of the particles decreased to 35.49 µm, with an upper limit size was 89.03 µm after sieving through 90 µm mesh. The biocomposites were subsequently tested for phage activity.

TABLE 9

Particle size and size distribution after grinding biocomposite on the basis of LMW-1L6.

| Measurement | Mean size (µm) ± SD | Lower limit size (µm) ± SD | Upper limit size (µm) ± SD |
|---|---|---|---|
| Right after grinding | 65.28 ± 6.393 | 10.21 ± 0.584 | 175.47 |
| After sieving through 90 µm mesh | 35.49 ± 4.532 | 8.86 ± 0.474 | 89.03 ± 1.432 |

To further optimize the process, a high-speed homogenizer was used to disintegrate the solid particles. The initial suspensions was prepared by mixing 2 g of $CaCO_3$, with mean particle size 6.2 µm, with 20 mL of water. Homogenization of the suspension for a period 15 sec and 5 min did not show a significant effect on particle size. Increasing the homogenization time to 15 min showed tangible effect where particle size decreased to 3.27 nm. Further increasing the homogenization time to 30 min gave only a slight diminishing particles size (3.10 nm). More details are provided in Table 10.

TABLE 10

Particles size and size distribution of $CaCO_3$ powder before and after the treatment with a high speed homogenizer. 2 g of $CaCO_3$ in 20 mL of water, at 22,000 rpm.

| Time of the treatment, min. | Particles mean size (µm) ± SD | Particles lower limit size (µm) ± SD | Particles upper limit size (µm) ± SD |
|---|---|---|---|
| Initial powder (as purchased) | 6.20 ± 0.013 | 1.99 ± 0.005 | 13.03 ± 0.057 |
| 0.25 | 5.59 ± 0.068 | 1.50 ± 0.015 | 12.23 ± 0.087 |
| 5 | 5.23 ± 0.043 | 1.54 ± 0.021 | 11.02 ± 0.198 |
| 15 | 3.27 ± 0.027 | 0.99 ± 0.016 | 6.79 ± 0.056 |
| 30 | 3.10 ± 0.026 | 0.95 ± 0.040 | 6.50 ± 0.114 |

This experiment showed that the high speed homogenizer can be used instead of mechanical grinding in a porcelain pounder for preparing bacteriophage loaded rough polymeric microparticles.

Preparation of Phage Loaded Microparticles

The preparation of rough polymeric microparticles (MPs) is a simple technology allowing for the encapsulation of bacteriophages and other phage products. In this embodiment, an insoluble inorganic salt (e.g. $CaCO_3$) containing adsorbed bacteriophages is added to a solution of LMW-1L6 in chloroform or DCM (or another organic solvent), the suspension is thoroughly homogenized, cast onto a hydrophobic surface, the solvent is evaporated, the fabricated brittle film is grinded and the obtained powder is sieved through 90 μm mesh-size sieve.

In addition to this technology we elaborated another simple technology which is based on the use of the insoluble inorganic salt (e.g. $CaCO_3$) with absorbed bacteriophages. According to the new technology the inorganic particles, "bearing" surface immobilized bacteriophages, are encapsulated ("wrapped") in the biodegradable polymeric capsule by oil-in-water (O/W)-solvent evaporation method.

In another embodiment, 0.1 g of the biodegradable polymer 8L6 was dissolved in 5 mL of DCM, 0.5 mL of water was added to this solution and homogenized at 10,000 rpm for 1 minute using a high-speed homogenizer, thus obtaining a polymeric emulsion. In a separate vessel 2 g of $CaCO_3$ with adsorbed phages was added to 50 mL of 2.5% PVA water solution and stirred for 20 min using a magnetic stirrer. The previously prepared polymeric suspension was added to the PVA solution in a drop-wise manner, while mixing at 22,000 rpm. After the emulsion was completely added, mixing was sustained for another 3 min. Afterwards, the obtained suspension was placed on a magnetic stirrer and stirred (450-500 rpm) for 4 h until the complete evaporation of DCM. Table 11 shows the size and size distributions of the obtained microcapsules. Resuspension of the microparticles following gravimetrical precipitation and freeze-drying did not change the properties of the microcapsules.

TABLE 11

The characteristics of MPs obtained by encapsulation of insoluble "bacteriophage bearing" inorganic particles ($CaCO_3$) in biodegradable amino acid based poly(ester amide) 8L6.

| # | The salt with adsorbed Phages, subjected to encapsulation with 8L6 | Mean diameter (μm) ± SD | Lower limit diameter (μm) ± SD | Upper limit diameter (μm) ± SD |
|---|---|---|---|---|
| 1 | $CaCO_3$ (as obtained) | 5.01 ± 0.01 | 1.67 ± 0.01 | 11.12 ± 0.08 |
| 2 | $CaCO_3$, re-suspended after self-precipitation (gravimetrically) | 5.55 ± 0.04 | 1.76 ± 0.01 | 11.82 ± 0.06 |
| 3 | $CaCO_3$, re-suspended after freeze-drying of the initial suspension (sample #1) | 5.02 ± 0.05 | 1.77 ± 0.01 | 10.06 ± 0.25 |

Standard protocol for determining activity of bacteriophages (in terms of plaque assay—PFU) for obtained solid preparations.

Determination of bacteriophage activity was obtained dissolving one gram of the solid in 4 mL of buffer at room temperature. The flask is placed on a shaker 30 min. and standard microbiological plaque assays are performed.

Activity of the $CaCO_3$ and $Ca_3(PO_4)_2$ with absorbed bacteriophages subsequently encapsulated in biodegradable poly(ester amide) 8L6 is given in Table 12.

TABLE 12

Insoluble calcium salts containing adsorbed bacteriophages encapsulated in the biodegradable poly(ester amide) 8L6.

| | Bacteriophage | PFU | | | |
|---|---|---|---|---|---|
| | | Initial phage concentrations TG1 solution | PFU of the bacteriophages desorbed from the encapsulated in poly(ester amide) 8L6 $CaCO_3$ salts | Initial phage concentrations in TG2 solution | PFU of the bacteriophages desorbed from the encapsulated in poly(ester amide) 8L6 $Ca_3(PO_4)_2$ salts |
| 1 | *Staphylococcus* | $10^8$ | $10^4$ | $10^9$ | $10^5$ |
| 2 | *E. coli* | $10^9$ | $10^6$ | $10^9$ | $10^7$ |
| 3 | *Streptococcus* | $10^8$ | $10^5$ | $10^8$ | $10^5$ |
| 4 | *Ps. aeruginosa* | $10^8$ | $10^5$ | $10^9$ | $10^6$ |
| 5 | *Proteus* | $10^8$ | $10^4$ | $10^8$ | $10^4$ |

Effect of Particle Size and Size Distribution

Inorganic salts such as calcium carbonate ($CaCO_3$) and calcium tri-phosphate ($Ca_3(PO_4)_2$) are used for preparing powdery preparation with adsorbed bacteriophages (see below). Those are vastly available and very cheap products. Purchasable calcium carbonate consists of microparticles of rather small size—mean size ca. 6 μm, and upper size 13 μm—both quite acceptable for preparing spray preparations for both medical and agricultural applications. We have found that after the treatment with high-speed homogenizer for 15 min particle size (both mean and upper sizes) could be diminished ca. twice (Table 13, sample #4).

TABLE 13

Particles size and size distribution of $CaCO_3$ powder before and after the treatment with HS-homogenizer at 22,000 rpm. 2 g of $CaCO_3$ in 20 mL of water.

| # | Time of the treatment, min. | Particles mean diameter (µm) ± SD | Particles lower limit diameter (µm) ± SD | Particles upper limit diameter (µm) ± SD | R* | Particles distribution |
|---|---|---|---|---|---|---|
| 1 | Initial powder (as purchased) | 6.20 ± 0.013 | 1.99 ± 0.005 | 13.03 ± 0.057 | 1.78 | wide |
| 2 | 0.25 | 5.59 ± 0.068 | 1.50 ± 0.015 | 12.23 ± 0.087 | 1.92 | wide |
| 3 | 5 | 5.23 ± 0.043 | 1.54 ± 0.021 | 11.02 ± 0.198 | 1.81 | wide |
| 4 | 15 | 3.27 ± 0.027 | 0.99 ± 0.016 | 6.79 ± 0.056 | 1.77 | wide |
| 5 | 30 | 3.10 ± 0.026 | 0.95 ± 0.040 | 6.50 ± 0.114 | 1.79 | wide |

*R = (Upper limit diameter − Lower limit diameter)/Mean diameter; R > 1.5 − wide particle distribution, R < 1.5 − narrow particle distribution.

The same was observed with calcium tri-phosphate. Commercial powders contained larger particles with mean size ca. 31 µm, and upper size ca. 59 µm. High speed homogenization for 3 min at lower speed 10,000 rpm reduced the size of the microparticles. The subsequent treatment up to 15 min led to a reduction of size with a mean diameter of 9.75 µm (mean) and an upper limit of 26.31 µm. More detailed results are found in Table 14.

TABLE 14

Particles size and size distribution of $Ca_3(PO_4)_2$ powder before and after the treatment in water with HS-homogenizer at 10,000 rpm. 2 g of $Ca_3(PO_4)_2$ in 20 mL of water.

| # | Time of the treatment, min. | Mean diameter (µm) ± SD | Lower limit diameter (µm) ± SD | Upper limit diameter (µm) ± SD |
|---|---|---|---|---|
| 1 | Initial powder (as purchased) | 30.97 ± 0.226 | 9.52 ± 0.051 | 59.29 ± 0.691 |
| 2 | 3 min | 16.38 ± 0.105 | 4.74 ± 0.043 | 37.41 ± 0.287 |
| 3 | 15 min | 9.75 ± 0.355 | 3.85 ± 0.029 | 26.31 ± 0.630 |
| 4 | PVA 3 min with 2.5% PVa (foam) | 55.68 ± 1.929 | 30.78 ± 0.021 | 85.01 ± 0.198 |
| 4 | #3 with subsequent mixing on a magnetic stirrer at 450 rpm for 3 h. A form partly disappeared | 22.91 ± 0.55 | 6.05 ± 4.83 | 50.54 ± 0.32 |

As was mentioned previously, water insoluble inorganic salts such as calcium carbonate and calcium phosphate strongly adsorb the bacteriophages from the solution. Our previous date were confirmed when working with cocktails of bacteriophages—TG-1 and TG-2.

The particles mean sizes of the commercial salts are of micrometer scale and can be directly used for preparing micro-emulsions. However, we have shown that, the particles sizes and size distribution can be narrowed after the treatment with a high-speed homogenizer. Owing to particles size the salts can be used as pulverizable solids (powders). Such form can be useful for dressing exudative wounds. Moreover, they can be prepared also as pulverizable liquids (i.e. pulverizable suspension) by mixing with PVA's or Poloxamer's solutions which solutions can be prepared on the basis of either liquid bacteriophages or saline solution as described hereinabove.

Example 5: Different Formulations for Different Applications

Non-limiting examples of applications for formulations containing encapsulated bacteriophages are provided below.

Formulation #1: Pulverizable Liquid

A simple and inexpensive pulverizable formulation for adhering bacteriophages on surfaces can be obtained by dissolving high-molecular-weight poly(vinyl alcohol) (PVA, MW 84,000-89,000 Da) in a bacteriophage solution at room temperature. For example, the concentration of the PVA is 2.5-5.0% (w/v). Spraying such preparations on surfaces (wound surface, plant surface, etc.) will allow the formation of an elastic PVA film impregnated with bacteriophages, after the evaporation of water. The PVA film will release phages as it can slowly dissolve in liquid found in the environment where it is sprayed/applied (bodily fluids, plants' irrigation system). This allows for a slow (prolonged) release of bacteriophages from the coating. The formulation can be loaded with other medicines (antibiotics, pain killers, hemostatics, etc.) along with bacteriophages.

An example of this formulation was prepared by dissolution of PVA (2.5% w/v; PVA content can be increased up to 5% or higher) in the liquid Phages TG-2 at room temperature and the obtained solution was kept in a refrigerator for three weeks. After three weeks PFUs of the phages of F1 were determined. The PFUs of the phages are retained at the initial level, in other words PVA did not inactivate Phages during three months.

Formulation #2: Pulverizable Liquid

Similarly, dissolving the Poloxamer 407 (P-407, MW 9,840-14,600 Da) in liquid bacteriophage solution at a temperature 5° C. An non-limiting example of P-407 concentration is 20% (w/v). Such preparation when being sprayed on warm surfaces (wound surface, plant surface, etc.) forms gel like coating impregnated with bacteriophages (in case of P-407 there is no need in water evaporation—the gelation takes place upon warming the formulation). The P-407 gel will release phages as it can slowly dissolve in liquid found in the environment where it is sprayed/applied (bodily fluids, plants' irrigation system). This allows for a slow (prolonged) release of bacteriophages. This formulation, due to the gel properties could be suitable for wounds, particularly for burns.

An example of the formulation #2 was prepared by dissolution of Poloxamer 407 (20% w/v) in the liquid preparation of phages TG-2 at room temperature and the obtained solution was kept in a refrigerator for three weeks. After three weeks PFUs of the phage of the F2 were determined. The concentration of the phages remained unchanged and equal to the initial level during three months.

The P-407 gel can be loaded with various medicines in combination with bacteriophages or phage products, and can be used for superficial wound healing purposes.

Formulation #3: Pulverizable Powder

Those are water insoluble salts like calcium and magnesium carbonates, calcium and magnesium phosphates (as well as their mixtures) containing surface adsorbed bacteriophages, in general labeled as St/BP. Other water insoluble salts of other metals such a barium, strontium, etc. can be used as well.

Formulation #4: Pulverizable Suspension

As noted above the St/BP can be used as pulverizable powders. However, in case it is desirable to fix the St/BP particles at surfaces (wound surface, plant surface, etc.), one can use formulations as suspensions of the St/BP in a solution of PVA in saline or liquid bacteriophage (2.5-5% (w/v) of PVA). Such formulation when being sprayed on the surface, forms an elastic film of PVA which is impregnated with the St/BP particles. The film of PVA will release phages as it can slowly dissolve in liquid found in the environment where it is sprayed/applied (bodily fluids, plants' irrigation system). This allows for a slow (prolonged) release of the St/BP particles. The formulation can be loaded with other medicines (antibiotics, pain killers, hemostatics, etc.) along with St/BPs.

Formulation #5: Pulverizable Suspension

To fix the St/BP particles at surfaces (wound surface, plant surface, etc.) the P-407 (or other poloxamers) can be used instead of the PVA. For example, formulations can be made as suspensions of the St/BP in a solution of the P-407 in saline or liquid bacteriophage solution (20%-25% (w/v) of the P-407 prepared at 5° C.). Such formulations when being sprayed on warm surfaces (wound surface, plant surface, etc.) form a gel-like coating impregnated with the St/BP particles (P-407 is in a liquid form at low temperatures but gels upon warming the formulation to bodily temperatures). P-407 gel will release phages as it can slowly dissolve in liquid found in the environment where it is sprayed/applied (bodily fluids, plants' irrigation system). This allows for a slow (prolonged) release of the particles with the adsorbed bacteriophages. The formulation can be loaded with other medicines (antibiotics, pain killers, hemostatics, etc.) along with St/BP.

Formulation #6: Pulverizable Powder

This product represents the St/BPs encapsulated in an amino acid based biodegradable polymer covered by the present patent application. The product is labeled as St/BP/En.

An advantage of encapsulating St/BPs encapsulated in an amino acid is to slow down the bacteriophage desorption from the salts, i.e. to make the desorption more controllable. Besides, the existence of the amino acid based biodegradable polymer is highly desirable when the product is used for wound healing processes as the polymer stimulates the wound healing, presumably through activating macrophages.

Formulation #7: Pulverizable Suspension

As noted above the St/BP/En can be used as pulverizable powders. However, if it is desirable to fix the St/BP/En particles on surfaces (wound surface, plant surface, etc.) formulations in the form of suspensions of the St/BP/En in a solution of PVA in saline or liquid bacteriophage (2.5-5% (w/v) of the PVA, for example) could be used. Such formulations when being sprayed on the surface form an elastic film of PVA which is impregnated with the St/BP/En particles. The film of PVA will release phages as it can slowly dissolve in liquid found in the environment where it is sprayed/applied (bodily fluids, plants' irrigation system). This allows for a slow (prolonged) release of the St/BP/En particles. The formulation can be loaded with other medicines (antibiotics, pain killers, hemostatics, etc.) along with St/BP/En.

Formulation #8: Pulverizable Suspension

To fix the St/BP/En particles on surfaces (wound surface, plant surface, etc.) the P-407 can be used instead of the PVA. Such formulations include for example suspensions of the St/BP/En in a solution of the P-407 in saline or liquid bacteriophage solution (20% (w/v) of the P-407 prepared at 5° C., non-limitingly). Such formulations, when sprayed on warm surfaces (wound surface, plant surface, etc.), form gel-like coating impregnated with the St/BP/En particles (in case of P-407 there is no need in water evaporation—the gelation takes place upon warming the formulation). The P-407 gel will release phages as it can slowly dissolve in liquid found in the environment where it is applied (bodily fluids, plants' irrigation system). This allows for a slow (prolonged) release of the St/BP/En particles. The formulation can be loaded with other medicines (antibiotics, pain killers, hemostatics, etc.) along with St/BP/En.

Formulation #9: Pulverizable Suspension

According to the W/O/W double emulsion method we elaborated, the suspension of microcapsules, also referred to as microspheres, with the bacteriophages in its interior (MS/BPI) suspended in a solution containing bacteriophages is obtained. This suspension can be used directly, without separating the MS/BPI from the surrounding liquid containing bacteriophages. The phages both entrapped in the MS/BPI and in the liquid phase (i.e. out of microspheres—in bacteriophage solution) will actively participate in the wound healing processes on two fronts: direct kill (provided by the free phages in the surrounding liquid) and prolonged release (provided by phages entrapped in the polymeric microcapsules). Such formulations (free of additive such as vehicles—PVA or P-407, see below) could be useful as a food additive. The formulation can be loaded with other medicines (antibiotics, pain killers, hemostatics, etc.) along with MS/BPI.

Formulation #10: Pulverizable Suspension

As noted above, the suspension of MS/BPI in the serial liquid bacteriophage can be used as pulverizable formulation. However, in case if there is a need to fix the MS/BPI particles at surfaces (wound surface, plant surface, etc.), it is possible to use formulations as suspensions of the MS/BPI in a solution of PVA. The formulations can be loaded with other medicines (antibiotics, pain killers, hemostatics, etc.) along with free bacteriophages and MS/BPI.

Examples of the Formulation #10 was prepared as follows: a water-in-oil-in-water (w/o/w) double emulsion-solvent evaporation method was employed to fabricate the biodegradable MSs with bacteriophages in the interior microcapsule space (i.e phages encapsulated in the biodegradable MSs). Briefly, the primary emulsion was prepared by 4.0 mL 1% w/v aqueous Kolliphor P188 (Surfactant 1) into 40.0 mL 5% w/v 8L6 in DCM and by homogenizing for 15 s at 10,000 rpm using a homogenizer (High shear strength disperse homogenizing emulsification machine C25). This primary emulsion was added to 100 mL of Phages TG-2, containing 2.5 or 5.0% of dissolved PVA with Mw=84,000-89,000 (Surfactant 2), and was homogenized for 3 min at 10,000 rpm. This w/o/w emulsion was immediately stirred using magnetic stirrer for 18 hours to evaporate organic solvent. The obtained suspension free of DCM was cast onto hydrophobized Petri-dishes and dried in a vacuum-drier at r.t. for 48 h over anhydrous $Na_2SO_4$ to remove water. The dried films containing both free phages and phages encapsulated in the biodegradable MSs were subjected to plaque assays to quantify phage concentrations. Phage activity was maintained after storage for at least one week.

In another example, a water-in-oil-in-water (w/o/w) double emulsion/solvent evaporation method was employed to fabricate bacteriophage loaded microspheres. Briefly, the primary emulsion was prepared by mixing 8 mL of 1% w/v water solution of Kolliphor P188 and 80 mL 5% w/v solution of poly(ester amide) 8L6 in dichloromethane (DCM) and by homogenizing for 15 s at 10,000 rpm. This primary emulsion was added to 200 mL bacteriophage concentrate (TG-2), containing 1% of low-molecular-weight polyvinyl alcohol (PVA, MW 13-23 KDa) and homogenized for 3 min at 10,000 rpm. This w/o/w emulsion was immediately moved to a magnetic stirrer and stirred for 24 hours to evaporate the organic solvent. Then prepared suspension was dialyzed against saline solution for 2 weeks and lyophilized over 48 h using TOPT-10C Freezing dryer, TOPTION, China (vacuum of 1 Pa, condenser—59° C., sample compartment+17° C.) and stored in a refrigerator.

Lytic activities of bacteriophages were measured after a month storage at 4° C. Bacteriophages were desorbed from the dried MSs according to the following protocol. 1.0 g of the freeze-dried MSs are placed in a flask and 4.0 mL of PBS at room temperature. The flask is placed on a shaker and shaken for 3 and 24 hours. After the shaking is stopped, the flask is kept for 5 min without agitation and aliquot is taken off from the supernatant for determining PFU.

Bacteriophages encapsulated in the MSs are active after one month storage in a refrigerator. Observed higher (by $10^1$-$10^2$) PFUs of the phages after 24 h shaking as compared with 3 h desorption could be ascribed to increasing the phages concentration in the liquid phase (saline solution) owing to the release of the phages from the MSs.

Formulation #11: Pulverizable Suspension

To fix the MS/BPI particles on surfaces (wound surface, plant surface, etc.) the P-407 can be used instead of the PVA, for example 20% (w/v) of the P-407 prepared at 5° C. Such formulation when being sprayed on warm surfaces (wound surface, plant surface, etc.) forms a gel-like coating impregnated with the MS/BPI particles. The P-407 gel gel will release phages as it can slowly dissolve in liquid found in the environment where it is applied (bodily fluids, plants' irrigation system). This allows for a slow (prolonged) release of the MS/BPI particles. The formulations can be loaded with other medicines (antibiotics, pain killers, hemostatics, etc.) along with free bacteriophages and MS/BPI.

Although the present invention has been described hereinabove by way of exemplary embodiments thereof, it will be readily appreciated that many modifications are possible in the exemplary embodiments without materially departing from the novel teachings and advantages of this invention. Accordingly, the scope of the claims should not be limited by the exemplary embodiments, but should be given the broadest interpretation consistent with the description as a whole. The present invention can also be modified, without departing from the spirit and nature of the subject invention as defined in the appended claims.

What is claimed is:

1. A composition comprising:
   polymer microcapsules;
   active bacteriophages encapsulated in the polymer microcapsules;
   wherein the polymer microcapsules include an amino-acid based polymer;
   wherein the active bacteriophages are adsorbed on inorganic particles encapsulated in the polymer microcapsules, the inorganic particles including particles of at least one salt selected from the group consisting of $CaCO_3$, $Ca_3(PO_4)_2$, $MgCO_3$, and $Mg_3(PO_4)_2$.

2. The composition as defined in claim 1, wherein the polymer microcapsules are in aqueous suspension.

3. The composition as defined in claim 1, wherein the inorganic particles have a mean size between 2 μm and 15 μm.

4. The composition as defined in claim 1, wherein the polymer microcapsules have a mean size between 20 μm and 100 μm.

5. The composition as defined in claim 1, wherein the polymer microcapsules have an upper limit size of 250 μm or less.

6. The composition as defined in claim 1, wherein the microcapsules are hollow and wherein a thickness of the polymer in the microcapsules is between 3% and 15% of the mean size.

7. The composition as defined in claim 1, wherein the amino-acid based polymer is selected from
   (1) a poly (ester amide urea) wherein at least one diol, at least one diacid, and at least one amino acid are linked together through an ester bond, an amide bond, and a urea bond,
   (2) a poly (ester urethane urea) wherein at least one diol and at least one amino acid are linked together through an ester bond, a urethane bond, and a urea bond,
   (3) a poly (ester amide urethane urea) wherein at least one diol, at least one diacid, and at least one amino acid are linked together through an ester bond, an amide bond, a urethane bond, and a urea bond,
   (4) a poly (ester amide urethane) wherein at least one diol, at least one diacid, and at least one amino acid are linked together through an ester bond, an amide bond, and a urethane bond,
   (5) a poly (ester urea) wherein at least one diol and at least one amino acid are linked together through an ester bond and a urea bond, and
   (6) a poly (ester urethane) wherein at least one diol and at least one amino acid are linked together through an ester bond and a urethane bond, further wherein the at least one diol is a compound of formula:

HO—R₁—OH,

R₁ is chosen from $C_2$-$C_{12}$ alkylene optionally interrupted by at least one oxygen, $C_3$-$C_8$ cycloalkylene, $C_3$-$C_{10}$ cycloalkylalkylene, , and , the at least one diacid is a compound of formula:

HO—(CO)—R₃—(CO)—OH, R₃ is $C_2$-$C_{12}$ alkylene, the at least one amino acid is chosen from naturally occurring amino acids and non-naturally occurring amino acid.

8. The composition as defined in claim 7, wherein the amino-acid based polymer is a poly (ester amide urea) comprising the following two blocks with random distribution thereof:

wherein the ratio of l:m ranges from 0.05:0.95 to 0.95:0.05, l+m=1,

R₁ is chosen from $C_2$-$C_{12}$ alkylenes optionally interrupted by at least one oxygen, $C_3$-$C_8$ cycloalkylenes, $C_3$-$C_{10}$ cycloalkylalkylenes, , or , R₃ is $C_2$-$C_{12}$ alkylene, R₂ and R₄ are independently chosen from the side chains of L- and D-amino acids so that the carbon to which R₂ or R₄ is attached has L or D chirality.

9. The composition as defined in claim 8, wherein the ratio of l:m ranges from 0.25:0.75 to 0.75:0.25, l+m=1.

10. The composition as defined in claim 8, wherein R₁ is —(CH₂)₆—, R₃ is —(CH₂)₈— and both R₂ and R₄ are the side chain of L-leucine.

11. The composition as defined in claim 1, wherein the amino-acid based polymer has a polydispersity of 1.15 or less.

12. The composition as defined in claim 1, wherein the amino-acid based polymer has a molecular weight between 15 kDa and 30 kDa.

13. The composition as defined in claim 1, wherein the amino-acid based polymer is amorphous.

14. The composition as defined in claim 1, wherein the active bacteriophages include at least two different strains of bacteriophages.

15. The composition as defined in claim 14, wherein the at least two different strains of bacteriophages include strains of bacteriophages from more than one family.

16. The composition as defined in claim 1, wherein the composition is liquid form and has a viscosity small enough to allow pulverization through a nozzle.

17. The composition as defined in claim 1, wherein the composition is powder form.

18. The composition as defined in claim 1, wherein the composition is in liquid form, and the polymer microcapsules are suspended in a solution including a poloxamer.

19. The composition as defined in claim 18, wherein the poloxamer is poloxamer 407.

20. The composition as defined in claim 19, wherein the poloxamer is in a concentration of between 10 and 30 percent.

21. The composition as defined in claim 19, wherein the poloxamer has a mean molecular weight of between 9500 kDa and 15000 kDa.

22. The composition as defined in claim 1, wherein the composition is in gel form.

23. The composition as defined in claim 1, wherein the polymer microcapsules contain on average more than 4 active bacteriophages.

24. The composition as defined in claim 1, wherein the polymer microcapsules contain on average more than 100 active bacteriophages.

25. The composition as defined in claim 1 wherein the composition further includes active bacteriophages outside of the polymer microcapsules.

26. The composition as defined in claim 25, further comprising a drug selected from the set consisting of antibiotics, pain killer and hemostatic drug.

27. The composition as defined in claim 1, wherein the composition comprises active bacteriophages, and wherein the composition has a stability such that at least 10% of the active phages remain active after storage of the composition for one year at 4° C.

* * * * *